United States Patent
Utterberg

(10) Patent No.: US 6,299,589 B1
(45) Date of Patent: Oct. 9, 2001

(54) FLOW-THROUGH TREATMENT METHOD

(75) Inventor: David S. Utterberg, Seattle, WA (US)

(73) Assignee: DSU Medical Corporation, Las Vegas, NV (US)

(*) Notice: Subject to any disclaimer, the term of this patent is extended or adjusted under 35 U.S.C. 154(b) by 0 days.

(21) Appl. No.: 09/038,375

(22) Filed: Mar. 11, 1998

Related U.S. Application Data

(62) Division of application No. 08/771,246, filed on Dec. 20, 1996, now Pat. No. 5,817,043, which is a division of application No. 08/373,598, filed on Jan. 17, 1995, now Pat. No. 5,643,190.

(51) Int. Cl.[7] .................................................. A61M 37/00
(52) U.S. Cl. ........................ 604/5.01; 604/4.01; 604/6.16; 604/6.01; 604/28; 604/32; 604/507
(58) Field of Search .................................. 604/4.01, 5.01, 604/5.02, 5.04, 6.16, 27–29, 500, 6.1, 6.11, 506–508; 210/645–46

(56) References Cited

U.S. PATENT DOCUMENTS

| | | |
|---|---|---|
| 3,861,388 | 1/1975 | Vaughn . |
| 3,994,293 | 11/1976 | Ferro . |
| 4,197,848 | 4/1980 | Garrett et al. . |
| 4,447,230 | 5/1984 | Gula et al. . |
| 4,493,705 | 1/1985 | Gordon et al. . |
| 4,559,043 | 12/1985 | Whitehouse et al. . |
| 4,654,026 | 3/1987 | Underwood . |
| 4,752,292 | 6/1988 | Lopez et al. . |
| 4,867,739 | 9/1989 | Kawano ................................ 604/4 |
| 4,871,353 | 10/1989 | Thomsen . |
| 4,966,585 | 10/1990 | Gangemi . |
| 4,976,685 | * 12/1990 | Block, Jr. . |
| 4,981,469 | 1/1991 | Whitehouse et al. . |
| 5,061,365 | * 10/1991 | Utterberg . |
| 5,078,699 | 1/1992 | Haber et al. . |
| 5,139,483 | * 8/1992 | Ryan . |
| 5,203,771 | * 4/1993 | Melker et al. . |
| 5,224,932 | * 7/1993 | Lappas . |
| 5,242,392 | * 9/1993 | Vaughn . |
| 5,330,425 | * 7/1994 | Utterberg . |
| 5,344,568 | 9/1994 | Kitaevich et al. ........................ 210/645 |
| 5,643,190 | 7/1997 | Utterberg . |
| 5,817,043 | 10/1998 | Utterberg ............................... 604/4 |
| 5,895,368 | 4/1999 | Utterberg ............................... 604/4 |

* cited by examiner

Primary Examiner—Angela D. Sykes
Assistant Examiner—Patricia Bianco
(74) Attorney, Agent, or Firm—Garrettson Ellis Seyfarth Shaw

(57) ABSTRACT

A flow-through blood treatment device such as a hemodialyzer comprises a housing, a blood inlet, a blood outlet, and at least one membrane in the housing defining a blood flow path between the blood inlet and outlet on one side of the membrane, plus a second flow path defined on the other side of the membrane. At least one of the blood inlet and outlet is connected to blood flow tubing, which blood flow tubing carries a connector spaced from the housing for access to the vascular system of a patient. The blood flow tubing also defines at least one connection site along its length permitting repeated, temporary connection and subsequent disconnection with branch conduits, for connection with sources of additive solutions or measuring devices. Typically, the blood flow tubing is free of permanently attached, flexible branch tubings a method of use in disclose.

15 Claims, 2 Drawing Sheets

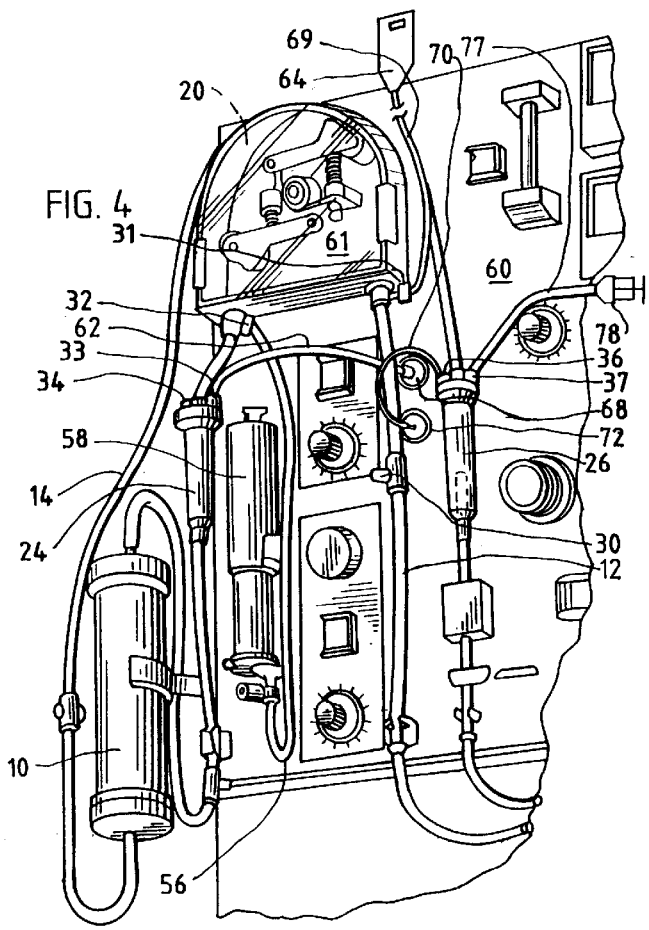
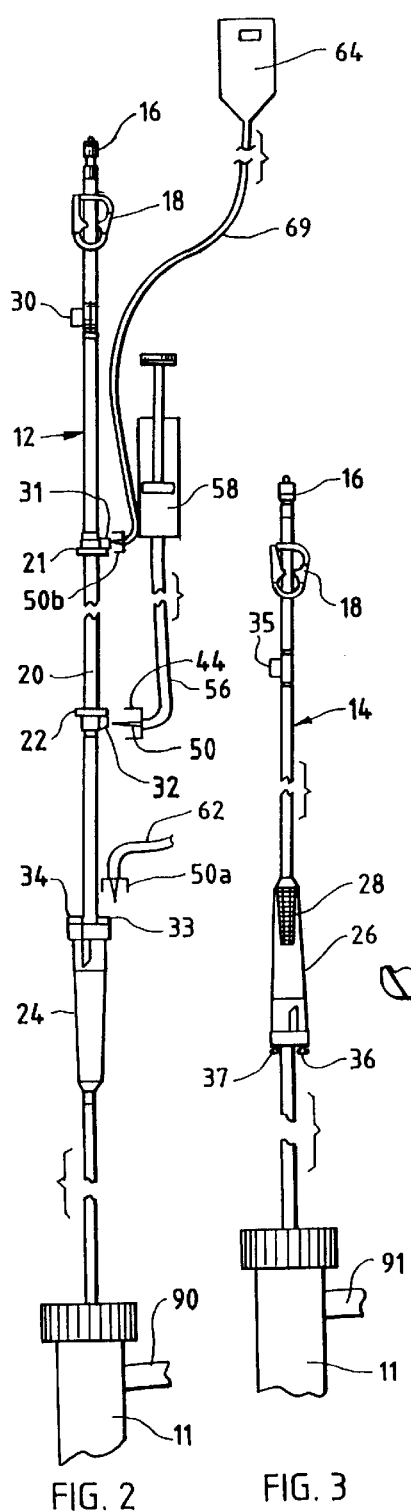
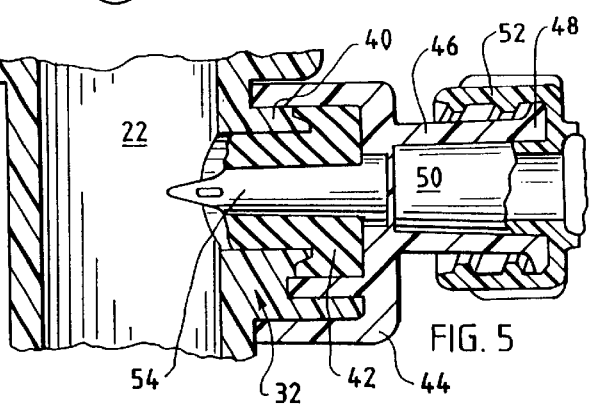
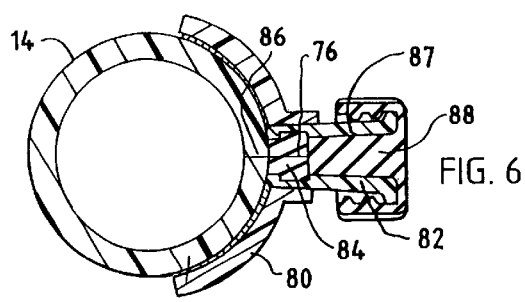
FIG. 2   FIG. 3   FIG. 4   FIG. 5   FIG. 6

FLOW-THROUGH TREATMENT METHOD

CROSS REFERENCE TO RELATED APPLICATION

This application is a divisional of application Ser. No. 08/771,246, filed Dec. 20, 1996, now U.S. Pat. No. 5,817,043, which is a division of application Ser. No. 08/373,598, filed Jan. 17, 1995, now U.S. Pat. No. 5,643,190.

BACKGROUND OF THE INVENTION

Blood treatment devices are extensively used in medicine, providing an extracorporeal blood circuit to direct blood to a treatment device from the patient, and then to return the blood to the patient. Some treatments involve separate, so called arterial and venous lines. Other treatment sets define a shared line to flow treated and untreated blood to and from the body.

The largest of this category in terms of the volume of use comprise devices having membranes in the flow treatment device. Such treatment devices include hemodialysis units, plasmapheresis units, hemofiltration units, and membrane-type blood oxygenators for open heart surgery. Also included are bubble-type oxygenators and other, more exotic blood treatment devices, where the blood may pass across a unit which carries a fixed bed of enzyme or other bioactive agent for various forms of blood treatment which are at the present time largely experimental.

While most reference herein will be directed to hemodialyzers, it is to be understood that other flow-through blood treatment devices are intended for modification in accordance with this invention.

The extracorporeal circulation of blood is a complex process. With hemodialysis, a membrane dialyzer is attached to a hemodialyzer hardware unit for providing dialysis solution, and controlling the parameters of blood flow through the membrane dialyzer. The dialyzer is connected at its respective arterial and venous blood flow ports with an arterial set and a venous set at one end of each, while the arterial and venous sets are connected to typically the fistula of a patient at the other set ends, to provide the circulatory flow path of blood from the patient, through the dialyzer, and back to the patient.

Such arterial and venous sets of the present technology carry connected branch lines, which connect the set to various important ancillary functions of the dialysis operation. Specifically, one of the branch connection lines connects with a source of anticoagulant such as heparin. This source typically comprises a syringe which may be controlled by the dialyzer hardware unit to provide a proper heparinization of the blood, to prevent clotting in the dialyzer or other blood treatment unit. Other branch lines connect with a pressure monitor(s). Another branch line from one of the sets typically connects with a container of intravenous quality saline solution for priming of the set, flushing it out, and for the emergency addition of saline to the patient in the event of a crisis brought onto the patient by excessive ultrafiltration.

Also, the sets may have a branch tubing extending from a blood chamber of the sets to which a syringe may be connected, to add or remove air to adjust the blood level in the chamber.

The present arterial and the venous sets are provided separately from the membrane dialyzer, and rather remind one of a spider web, being complex to manufacture and complex to set up in the clinic.

Traditionally, the known blood tubing sets have exhibited disadvantages including the following:

Conventional sets for flow-through blood treatment devices such as hemodialyzers are typically expensive to manufacture. The two dialysis sets needed for a conventional hemodialysis may have more than twenty feet of tubing and over seventy parts, which must be assembled together in a multi-axis array because of the requirement for branch tubings and the like. Thus, the cost effective automation of the manufacture of such sets is not practical, due primarily to the number of components in the sets and the complexity of the various branch connecting tubes which come off of the blood pathway tubing.

A reason that such conventional sets for blood handling are expensive and complex is that they generally must be set up to receive every user-connected ancillary device that a physician might prescribe. However, less than the maximum number of such ancillary devices are typically prescribed in any given treatment, so that some of the branch tubings or other connectors go unused. However, due to the difficulty of stocking and manufacturing the wide variety of different designs that would be required if sets were made for each different physician-dictated procedure, the wasteful practice of providing all branch tubings that may possibly ever be needed is tolerated. To do that is cheaper than administering the vast number of alternate design sets that would otherwise have to be provided.

As a further disadvantage, the branch tubings and connectors extending off of the blood tubing can each tend to provide a stagnant site for blood to collect, which can aggravate clotting problems. By this invention, these stagnant sites can be substantially eliminated from the branch connections which are present.

Also, most branching and ancillary lines of blood handling sets include an on/off tubing clamp to isolate the blood pathway, with these tubing clamps being clamped or manipulated during the dialysis procedure. Such clamps are relatively expensive, and are prone to misclamping errors such as partial clamping or accidental, spontaneous opening. Thus, a branching ancillary line of a conventional blood handling set may accidentally open during a dialysis procedure, for example, when the branching line is not even connected to anything. This of course may result in the spilling of blood in positive pressure sections of the blood pathway, and unsterile air incursion into negative pressure blood pathway sections.

Also, just as the conventional blood handling sets are expensive to manufacture, they are time consuming for similar reasons to prepare for use. As a further disadvantage, the conventional blood handling sets are not cost effectively reused because of their complexity, and also because of the stagnant blood which can clot in the branch lines.

Also, conventional blood lines carry elastomeric injection sites which communicate with the blood flow pathway, for blood sampling or medicament infusion via a syringe and needle. It is known for these injection sites to have been put to emergency service as an access for pressure monitoring and the like via a needle which is connected to a tube communicating with a pressure monitor or the like. This occurs when a permanently connected branch tube has clotted or otherwise failed.

This prior art has many disadvantages. The above needle is exposed and dangerous. Also, the needle is not lockable to prior art, unlockable injection sites, and often falls over even when taped. The injection site cannot then be used for its original purpose. The prior art injection site is not placed where heparin infusion, arterial post pump monitoring, etc. is best accomplished.

DESCRIPTION OF THE INVENTION

By this invention, a set for a flow-through blood treatment device such as a dialyzer is provided in which the branching, ancillary lines of the set are typically each replaced with a branch replacing locking connection site. Such a modified blood handling set is more easily manufactured, and is more susceptible to automated manufacture because part-to-part automation is more advanced and cheaper than part-to-tube automation and clamp-to tube automation. The branching lines are thus eliminated and replaced with one or more connection sites. Then, as needed, a separable locking, branch line or other locking connection scheme with an ancillary device can be made through a branch replacing, locking connection site, to adapt the blood set to the particular medical procedure. Some branch replacing, locking connection sites on the blood set may remain unused, and they can be designed to avoid a stagnant area, as was inevitable with an integrally attached branch line.

Such connection sites may be carried on the tubing of the blood set, and/or they may be carried on blood degassing chambers (either communicating with the air space or blood space of said chambers), which are commonly provided in-line between sections of blood tubing of the set. Such connection sites may comprise injection sites (with or without pre-split septums), stop cocks, or locking luers, preferably female luers which carry a resealable, needle puncturable diaphragm adjacent its inner end or a valve adjacent its inner end. The connection sites typically carry a locking feature.

During the flow-through blood treatment procedure or after termination, the branch lines or devices may be once again removed, preferably making use of sealing means of the branch replacing, locking connection sites. After termination, the inventive blood sets and/or the separable branch lines (whether or not connected to the blood sets) may be processed for reuse by conventional means.

The blood treatment device may, if desired, be permanently connected as manufactured to a blood set or sets for supplying blood to it and for conveying processed blood back to the patient, with the entire system of the treatment device and at least one of the blood sets being washed in a conventional manner and stored for reuse, with or without the inventive separable branch lines, or devices connected during processing or storage. Preferably, new branch lines and ancillary devices would be used for each procedure. Thus, by this invention, blood handling sets can become more reusable, by being flushed and cleaned with chemical, heat or other means, between uses along with the blood treatment device to which they may permanently connect, or be separately processed for reuse if desired, partly because of the great reduction of stagnant flow sites where blood clots form or chemicals accumulate because of the presence of branch replacing, locking connection sites rather than branching tubing in the sets. Also, the separable locking branch lines may be reused or (preferably) not.

Accordingly, this invention provides a flow-through blood treatment device which comprises: a housing, a blood inlet, a blood outlet, typically at least one membrane defining a blood flow path between the blood inlet and outlet on one side of the membrane, and a second flow path defined on the other side of the membrane. At least one of the blood inlet and outlet, and preferably both, are connected to blood flow tubing in which the blood flow tubing carries a connector, spaced from the housing, for access to the vascular system of a patient.

On the other hand, the blood treatment device may not carry a membrane, and may include, for example, charcoal or a resin bed for blood treatment. Also, this invention can apply to blood treatment devices in which the blood inlet and the blood outlet is the same, with a single blood flow tubing attached to the combined inlet-outlet in which the blood flow tubing carries a connector, spaced from the blood treatment device, for access to the vascular system of a patient.

The blood flow tubing defines at least one branch replacing, locking connection site along its length, and preferably a plurality thereof, which connection site permits repeated, temporary connection and subsequent disconnection with devices, or with branch conduits for connection with sources of additive solutions or for connection with measuring or sampling devices. Thus, the blood flow tubing can be mostly free of permanently attached, flexible branch tubings, which create the known disadvantages both in manufacture, setup, use, and reuse.

The connection of the blood flow tubing can be either permanently or separably connected with the blood treatment device. Preferably, both the blood inlet and outlet of the blood treatment device are permanently connected with the blood flow tubing of the type described above to facilitate reuse of both units.

The blood flow tubing may define various components along its length other than just uniform, cylindrical tubing. For example, the blood flow tubing may define one or more pumping device fitments such as a roller pump tubing section, which is typically of larger diameter than other sections of the blood flow tubing, as is conventional, or a diaphragmatic pumping device, a turbine pumping device, or other segment or device capable of pumping blood in a manner suitable to the extracorporeal procedure required. Also, one or more blood chambers may be provided in the blood flow tubing to serve as a degassing chamber, and also to typically carry one or more branch replacing, locking connection sites in accordance with this invention, thus avoiding permanently connected branch tubing as is currently conventional in dialysis sets and the like.

Preferably, at least some of the branch replacing, locking connection sites may comprise a pierceable elastomer, resealable diaphragm in one of many known designs to receive a spike or needle for providing connection with a device or a separate branch conduit, which may be a flexible length of tubing leading to an ancillary unit of some kind. Alternatively, the elastomer diaphragm may be slit for ease of entry with a blunt tipped connector member such as a locking male luer or a blunt-tipped hollow spike. Preferably, the elastomeric injection site moving will also comprise locking means whether by spike, luer locking, bayonet, snap-fit-lock methods, or the like. Specifically, a plastic universal connector may be used for connection through the diaphragm in accordance with U.S. Pat. No. 5,071,413. By this design a luer lock connection may be provided between each connection site and a temporary device or branch conduit which is terminated with a universal connector of the type described. Also one may use a valve that may be opened by a particular pressure, or by mechanical opening such as by fitment or a male luer.

Such connection sites may preferably comprise a female luer connector which, in turn, comprises a hollow body defining a frustoconical bore having a larger and a smaller end, for receiving a needle, a spike, or a frustoconical male luer connector in the frustoconical bore. An elastomeric, penetrable, resealable partition is carried by the hollow body to occlude the bore adjacent the smaller end. The body communicates with the blood tubing, which carries the connection site adjacent the smaller end. Such a structure can accommodate varying types of male luer lock connectors as well as various spike connectors, or an injection needle.

Thus, it becomes possible to perform an extracorporeal blood treatment which comprises: connecting a flow-through blood treatment device with the vascular system of a patient through arterial and venous blood tubings connected to the device. At least one of the blood tubings, and preferably both, are typically free of permanently attached, flexible branch tubings, and carry at least one branch replacing locking connection site along its length. One then connects a first locking device and/or a branch conduit to the one branch replacing connection site, with the first device comprising, or the first branch conduit being connected to, typically, one of the following ancillary units: a source of anticoagulant solution, a source of blood-compatible solution, a pressure monitor, or a syringe. One then performs the extracorporeal blood treatment by flowing blood through the treatment device and the connected blood tubings.

Preferably, a second locking device and/or a branch replacing, locking conduit is provided to a second branch replacing, locking connection site on one of the blood tubings, including the step of connecting the second device, or connecting the second branch conduit, to one of the above ancillary units, which unit is of a different type from the unit connected with the first branch conduit.

An example of a locking device recited above is a heparin source carried as a part of a dialysis machine and having a connector such as a locking spike that can engage one of the branch, replacing, locking connection sites. A locking spike is illustrated below. Also, the term "branch conduit" as used below is intended to include such locking devices, which necessarily must comprise at least a short conduit.

Following the extracorporeal blood treatment, one disconnects the locking devices and/or branch conduits from the blood tubings which connect to the blood treatment device. One preferably stores the blood treatment device for reuse while the device remains connected with at least one of the blood tubings, and preferably both, when present.

Thus, one or both of the blood tubings may be free of permanently attached branch tubings, to achieve the advantages discussed above.

DESCRIPTION OF DRAWINGS

Referring to the drawings,

FIG. 2 is a plan view of an arterial blood set, connected to a hemodialyzer and designed in accordance with this invention;

FIG. 3 is a plan view of a venous blood set shown connected to the opposite end of the same hemodialyzer as shown in FIG. 1;

FIG. 4 is a perspective view of the apparatus shown in FIGS. 2 and 3, mounted on a conventional hemodialysis machine for use;

FIG. 5 is a magnified, longitudinal sectional view of a branch connector carried on a blood set in accordance with this invention, showing its connection with a locking type male luer spike connector carried on branch tubing; and FIG. 6 is an enlarged transverse section taken along a plane of 90 degrees from the section of FIG. 5, and showing another design of branch connector of a blood set, in a sealed mode.

DESCRIPTION OF SPECIFIC EMBODIMENTS

Figure 1:
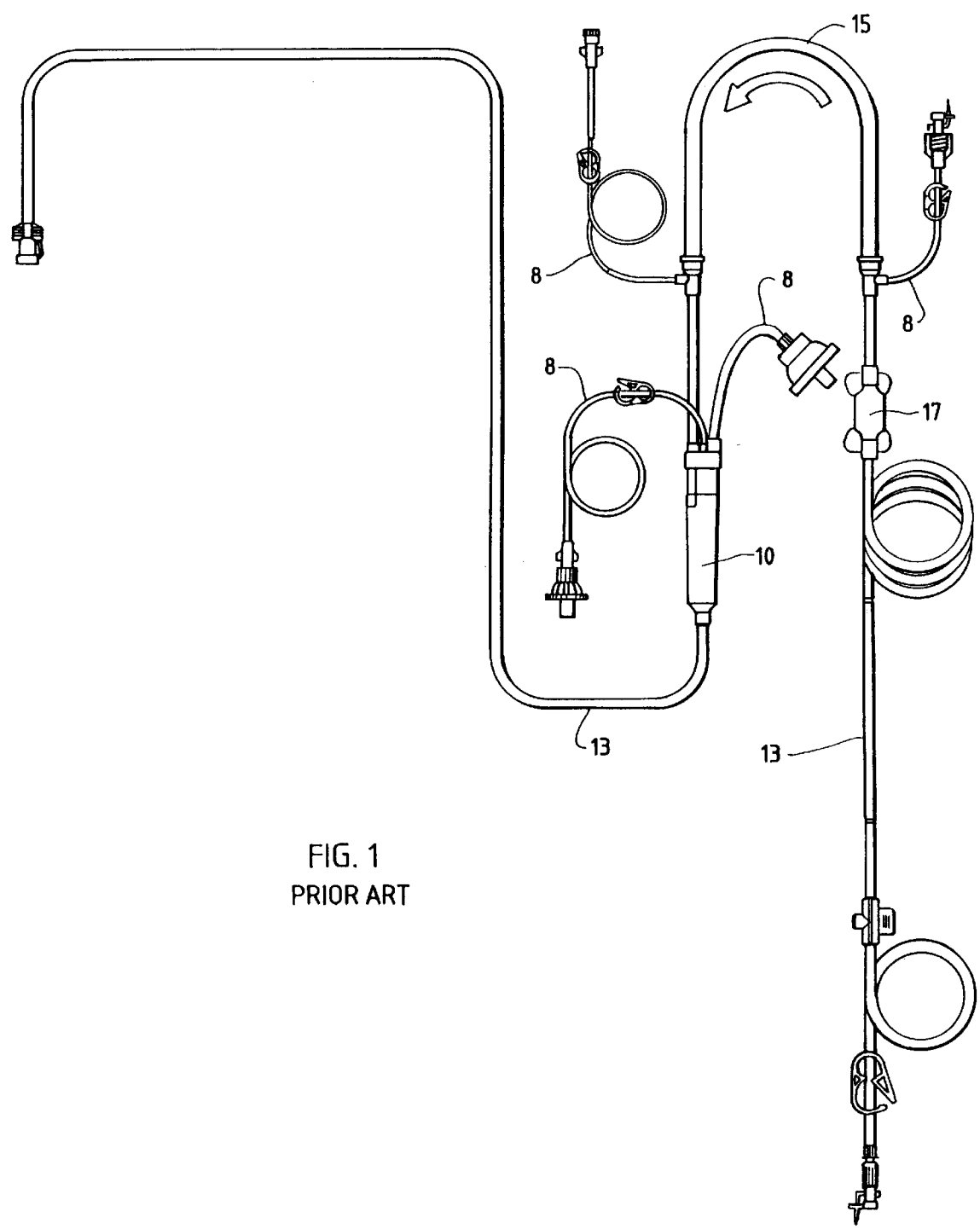
FIG. 1 is a conventional dialysis set with permanently bonded branch lines and non-locking injection sites for sampling and medicament injection.

Referring to FIG. 1, a conventional arterial set for a hemodialyzer is shown, having permanently connected branch lines 8 branching off of the tubular set 13 in various positions as shown. The debubbling chamber 10 also carries branch lines 8. The set also carries conventional roller pump tubing 15, and other, conventional parts such as pressure pillow 17.

Referring to the FIGS. 2–4, a hemodialyzer 11 is shown, illustrative of the class of flow-through blood treatment devices to which this invention pertains.

FIG. 2 shows an arterial blood set 12, while FIG. 3 shows a venous blood set 14, each of the blood sets respectively communicating with the blood flow path through hemodialyzer, 11 and permanently or temporarily connected to the hemodialyzer at opposed ends thereof.

Each of blood sets 12, 14 may be of conventional design except as otherwise indicated herein. Each of sets 12, 14 may carry a conventional fistula connector or other connector 16 at its end opposed to the end connected to hemodialyzer 11. A conventional flow clamp 18 may be provided to each set as well.

Arterial set 12 may carry a conventional length of roller pump tubing 20, connected at its ends to other lengths of tubing of the set 12 through appropriate connectors 21, 22, which are modified in accordance with this invention to carry a connection site 31 or 32.

Each of sets 12, 14 also carry a bubble trapping chamber 24 or 26 respectively. Venous chamber 26 typically carries a conventional filter 28. As an alternative design, the venous chamber 26 may be replaced with a bubble trapping chamber of the type disclosed in U.S. Pat. No. 5,328,061. The arterial chamber 24 may also be replaced with a chamber of similar design except typically without the added filter.

The respective sets, 12, 14 may preferably be permanently connected to respective ends of dialyzer 10, although a conventional temporary connection system may be used if desired. The dialyzer and the sets 12, 14 may be effectively flushed and reused as a single unit (or otherwise separately) in accordance with otherwise conventional reuse procedures, because of the absence of permanently attached, flexible branch tubings on the sets.

In accordance with this invention, sets 12, 14 carry a plurality of branch replacing, locking connection sites 31–34 and 36–37 at various locations between the set ends. Conventional injection sites 30 and 35 are carried along a length of the respective tubing of the sets 12, 14. Branch replacing, locking connection sites 31, 32 may be carried on the tubing or preferably by the connectors 21, 22 which connect the flow through pumping tubing 20 with the remainder of the set tubing. Branch replacing connection sites 33, 34, 36 and 37 may be carried on the respective bubble trapping chambers 24, 26 of the sets. They may all be of broadly similar designs to the types shown in FIGS. 5 and 6.

Referring to FIGS. 5 and 6, the specific designs of the respective connector members may be all relatively similar except for obvious modifications due to their positioning.

In FIG. 5, connector 31 is shown in detail. There, a short side port 40 extends outwardly from the main tubing of set 12 carried on connector 22. Side port 40 carries an elastomeric, spike-penetratable, resealable partition 42 which extends inwardly to the lumen of side port 40, to substantially prevent the formation of any substantial recess which might cause stagnant blood from flow through set 12 to collect and clot.

An outer body 44 is provided, enclosing elastomeric partition 42 and typically placing it under pressure. Outer body 44 is then sealed by heat sealing, snap fit, or the like to tubular port 40.

Preferably, outer body 44 also defines a female luer site 46 which is typically in compliance with typical medical requirements such as the ANSI specifications for luer connectors. Female luer 46 defines a series of radial outer projections 48 at its outer end. Thus, a spike connector of any of various designs can be used to provide communication through this connector to the flow path of set 12. While a needle may be also used to penetrate elastomeric partition 42, it is preferred to use a plastic spike connector 50 having a relatively blunt tip to prevent accidental needle sticks, for example the MEDIC® spike, sold by the Medisystems Corporation of Seattle, Washington, covered by U.S. Pat. No. 5,071,413. Such a connector provides a strong, positive, mechanical lock between substantially rigid parts through a threaded luer lock member 52, which can engage the substantially rigid projections 48 of the female luer 46 while providing a luer connection, but without relying only on frictional locking. At the same time, the spike 54 of the penetrating connector provides reliable flow communication with the blood flow path of set 12.

While the releasable but positive mechanical lock between substantially rigid parts as shown herein comprises a threaded luer lock member 52, alternative positive mechanical locks of known variety may be used as a substitute or an equivalent thereto, for example, a bayonet coupling, or a click lock connection having projecting longitudinal connector arms, (as is used in the well-known Sarns connector). Because of the use of such positive mechanically locked connections, the prior art technique of taping together a needle entering a Y connector and further taping the connection to the skin, is not required, for saving time, improving patient comfort, and increasing reliability.

As shown in FIG. 2, a spike connector 50 is connected to branch tubing 56 which, in turn, connects with a conventional syringe of heparin solution 58. Spike connector 50 may connect with branch connector 32 as illustrated in FIG. 2 and also FIG. 4, where the dialyzer 10 and sets 12, 14 are mounted on a dialysis machine 60. Heparin syringe 58 is mounted in a heparin administration unit of the dialyzer machine 60, and branch line 56 is connected with branch replacing connector 32 by means of spike 50 in a manner similar to FIG. 5.

Another spike 50a, carried by branch line 62, may connect with set 12 (FIG. 2) through branch replacing connector 33 carried on the bubble trapping chamber 24, to provide connection with a pressure monitoring instrument connection 68 or the like. Branch connector 31 may be used to connect a branch line 69 via spike 50b to for saline solution 64.

Added branch replacing connections may be made in similar manner, using respective branch replacing connectors 34, 36, and 37. For example, a separable branch line 70 (FIG. 4) may connect with connector 36 of chamber 26 to provide connection with pressure monitor 72, which is carried by the dialyzer machine 60. Another branch connection line 77 may temporarily connect through branch connection site 37, carried on chamber 26, to a syringe 78 for raising or lowering the blood level in chamber 26.

Typically dialyzer 10 and sets 12, 14 are mounted on the dialyzer machine 60 in the typical manner, with roller pump tubing 20 being mounted in flow-through pumping means, specifically roller pump 61. Then, the respective branch lines 56, 62, 69, 70, 77 can be added by selecting any of the branch replacing connection sites 31–34 and 36–37 as may be most convenient. It can be seen that not all of the branch replacing connection sites are necessarily used, leaving room for added functions, or for sample withdrawal by a simple needle. Also, branch connection sites carried on the chambers 24, 26 can be used to connect with a syringe connected to branch tubing, for adjustment of the size of the air bubble captured within the chamber, for sample collection, or for addition of medication, in conventional manner.

Thus, dialyzer 10 and the attached sets 12, 14 may be modified in their configuration by the selective addition of any desired branch lines for use in any desired variety of dialysis procedures, depending upon the preference of the doctor and the needs of the patient.

If desired, partition 42 may carry a normally closed transverse slit, so that blunt-tipped connectors may be used for penetration through the respective branch replacing, locking connector sites 31–34 and 36–37.

FIG. 6 shows an alternate design of branch connector 31–34 or 36–37, which may be used for connection to a set in accordance with this invention. The tubing of set 14, for example, may carry in sealed relation a saddle-like mounting structure 80, sealed to tubing 14. Mounting structure 80, in turn, carries a female luer housing 82 which carries an elastomeric partition or plug 84 at the inner end of luer housing 82 i.e., the narrow end of the tapering bore thereof. Elastomeric partition 84 may carry a slit 76 to facilitate penetration by a blunt tipped male connector. Also, a second slit 86 may be formed in the flexible wall of the tubing 14, being sealed from the exterior by the seal of the saddle-like retention member 80. Alternatively, a hole may replace slit 86.

The branch connector may be temporarily closed by a luer lock plug 88, which may be of a single molded piece if desired. Plug 88, and/or elastomeric partition 84 may be impregnated with an antiseptic such as iodine or the like, or antiseptic added to the tapered bore 87, so that while luer lock plug 88 is in position, the tapered bore 87 and at least the outer surface of elastomeric partition 84 may be exposed to antimicrobial conditions between uses.

Thus, the branch replacing connector sites 31–34 and 36–37 on the respective sets may be reused for a substantial number of times. After the withdrawal of each penetrating spike 50, an antiseptic-impregnated locking plug similar to plug 88 may be applied for the substantial resterilization of the system between uses.

Alternatively, a valve arrangement may be used as one or more of sites 31–34 and 36–37, for example a valve as shown in Brimhall et al. U.S. Pat. No. 5,242,393, or otherwise a "stopcock" arrangement.

After the dialysis procedure is complete, the blood is flushed in a conventional manner from dialyzer 10 and sets 12, 14, typically making use of saline solution of container 64. Then, the various temporary branch lines 56, 62, 69, 70, 77 may be removed, along with their spikes 50. Locking plugs 88, when used, may be reapplied to the respective branch connection sites, and the connected dialyzer and sets 12, 14 are ready for cleaning and storage for reuse.

As is conventional, a bleach or formaldehyde solution or other disinfectant is passed through the system. A pressure differential is often used to flush cleaning solution through the membrane of the hemodialyzer 10, and the dialysis flow path of the membrane dialyzer 10 may be conventionally cleansed by flushing through dialysis solution ports 90, 91.

Good cleaning of the connected sets 12, 14 can take place because the flow is substantially linear through the sets, since the respective branch lines have been removed.

Then, when the dialyzer and attached sets have been properly cleaned, they are filled with a disinfectant/storage solution and put away for the next use.

Thus, an improved, flow-through blood treatment device is provided which is easier to set up and cheaper. Also, it may be cleansed and reused with greater facility and ease, resulting in reduced cost of operation.

The above has been offered for illustrative purposes only, and is not intended to limit the scope of the invention of this application, which is as defined in the claims below.

That which is claimed is:

1. The method of performing an extracorporeal blood treatment, which comprises:

connecting a flow through blood treatment device with the vascular system of a patient through at least one blood tubing connected to said device, said blood tubing being free of permanently attached, flexible branch tubings and carrying at least one branch connection site along its length;

connecting a first branch conduit to said one branch connection site, said first branch conduit also being connected to a first ancillary unit comprising a source of anticoagulant solution, a source of blood-compatible solution; or a pressure monitor, and performing said extracorporeal blood treatment by flowing blood through said device and connected blood tubing.

2. The method of claim 1 including the step of connecting a second branch conduit to a second branch connection site on said blood tubing, and also connecting said second branch conduit to a second ancillary unit comprising a source of blood-compatible solution, a pressure monitor, or a source of anticoagulant solution, said second ancillary unit being of different type from the first ancillary unit.

3. The method of claim 2 further comprising the steps of disconnecting said first and second branch conduits from said blood tubing after said extracorporeal blood treatment, and storing the blood treatment device for reuse while said device remains connected with said blood tubing.

4. The method of claim 1 further comprising the steps of disconnecting said first branch conduit from said blood tubing after said extracorporeal blood treatment, and storing the blood treatment device for reuse while said device remains connected with said blood tubing.

5. The method of claim 4 in which said blood treatment device is connected to a pair of said blood tubings respectively for blood inflow and outflow, said blood tubings being both free of permanently attached, flexible branch tubings, and each carry at least one of said branch connection sites, and including the step of connecting a second branch conduit to the blood tubing other than the blood tubing to which the first branch conduit is connected.

6. The method of performing hemodialysis, which comprises:

connecting a membrane dialyzer with a hemodialysis machine, said membrane dialyzer being connected with arterial and venous blood tubings, said blood tubings being free of permanently attached, flexible branch tubings, each of said blood tubings carrying at least one connection site along their lengths;

connecting a first branch conduit to the connection site of one of said blood tubings and connecting a second branch conduit to the connection site of one of said blood tubings; connecting each of said branch conduits to a source of anticoagulant solution, to a source of saline solution; or to a pressure monitor, and performing hemodialysis with said membrane dialyzer.

7. The method of claim 6 further comprising the steps of disconnecting said first and second branch conduits from the blood tubings after said hemodialysis, and storing the membrane dialyzer for reuse while remaining connected with said blood tubings.

8. The method of claim 7 in which said blood tubings each carry respective blood degassing chambers along their length, plus the step of connecting a third of said branch conduits with one of said blood tubings through a branch connector carried on said degassing chamber, the third branch conduit being also connected with a pressure monitor.

9. The method of performing an extracorporeal blood treatment, which comprises:

connecting a flow-through blood treatment device with the vascular system of a patient through arterial and venous blood tubings connected to said device, said blood tubings carrying at least two branch connection sites in total along their lengths;

connecting a first branch conduit to one of said branch connection sites and providing a positive mechanical lock between a substantially rigid part of said connection site and a substantially rigid portion of the connected branch conduit, said first branch conduit also being connected to a first ancillary unit comprising a source of anticoagulant solution, a source of blood compatible solution, or a pressure monitor; connecting a second branch conduit to a second branch connection site on one of said blood tubings, using a connection having a positive mechanical lock between a substantially rigid part of said connection site and a substantially rigid portion of said connected second branch conduit, and also connecting said second branch conduit to a second ancillary unit comprising a source of blood-compatible solution, a pressure monitor, or a source of anticoagulant solution, said second ancillary unit being of a different type from the first ancillary unit; and, after said extracorporeal blood treatment, disconnecting said first and second branch conduits from said blood tubings, and storing the blood treatment device for reuse while said device remains connected with at least one of said blood tubings.

10. The method of claim 9 in which said blood tubings are free of permanently attached, flexible branch tubings, and each carry at least one of said branch connection sites.

11. The method of claim 9 in which at least one of said first and second branch conduits are previously permanently connected respectively to said first and second ancillary units.

12. The method of claim 2 in which at least one of said first and second branch conduits are previously permanently connected respectively to said first and second ancillary units.

13. The method of claim 1 in which said first branch conduit is connected to a source of saline solution or a source of heparin solution.

14. The method of claim 6 in which said anticoagulant solution is heparin solution.

15. The method of claim 9 in which said first branch conduit is connected to a source of saline solution or a source of heparin solution.

* * * * *

UNITED STATES PATENT AND TRADEMARK OFFICE
CERTIFICATE OF CORRECTION

PATENT NO. : 6,299,589 B1
DATED : October 9, 2001
INVENTOR(S) : Utterberg

Page 1 of 1

It is certified that error appears in the above-identified patent and that said Letters Patent is hereby corrected as shown below:

<u>Title page,</u>
Item [56], References Cited, add
-- 5,693,008*     12/1997     Brugger et al. --.

Item [57], ABSTRACT, last line, "in disclose" should be -- is disclosed --.

<u>Column 9,</u>
Line 27, "solution;" should be -- solution, -- and "monitor," should be -- monitor; --.

<u>Column 10,</u>
Line 3, "solution;" should be -- solution, -- and "monitor," should be -- monitor; --.

Signed and Sealed this

Fourteenth Day of May, 2002

*Attest:*

*Attesting Officer*

JAMES E. ROGAN
*Director of the United States Patent and Trademark Office*